(12) United States Patent
Poulsen

(10) Patent No.: US 10,507,023 B2
(45) Date of Patent: Dec. 17, 2019

(54) SELF-CENTERING SPIRAL FILTER

(71) Applicant: Cook Medical Technologies LLC, Bloomington, IN (US)

(72) Inventor: Andreas Poulsen, Borup (DK)

(73) Assignee: Cook Medical Technologies LLC, Bloomington, IN (US)

( * ) Notice: Subject to any disclaimer, the term of this patent is extended or adjusted under 35 U.S.C. 154(b) by 127 days.

(21) Appl. No.: 15/689,624

(22) Filed: Aug. 29, 2017

(65) Prior Publication Data
US 2018/0103960 A1  Apr. 19, 2018

Related U.S. Application Data

(60) Provisional application No. 62/409,917, filed on Oct. 19, 2016.

(51) Int. Cl.
*A61M 29/00* (2006.01)
*A61B 17/12* (2006.01)
*A61F 2/01* (2006.01)

(52) U.S. Cl.
CPC .. *A61B 17/12109* (2013.01); *A61B 17/12145* (2013.01); *A61F 2/01* (2013.01); *A61F 2002/016* (2013.01); *A61F 2230/0091* (2013.01)

(58) Field of Classification Search
CPC .............. A61F 2/01; A61F 2002/016; A61F 2230/0091; A61B 17/12109; A61B 17/12113; A61B 17/1214; A61B 17/12145
See application file for complete search history.

(56) References Cited

U.S. PATENT DOCUMENTS

| | | | |
|---|---|---|---|
| 5,893,869 A | | 4/1999 | Barnhart et al. |
| 6,059,825 A | * | 5/2000 | Hobbs ........................ A61F 2/01 623/1.18 |
| 6,171,338 B1 | | 1/2001 | Talja et al. |
| 7,018,401 B1 | | 3/2006 | Hyodoh et al. |
| 8,162,970 B2 | | 4/2012 | Gilson et al. |
| 2007/0239199 A1 | * | 10/2007 | Jayaraman ................ A61F 2/01 606/200 |
| 2008/0183206 A1 | | 7/2008 | Batiste |
| 2009/0216263 A1 | * | 8/2009 | Tekulve ........... A61B 17/12022 606/200 |
| 2012/0010650 A1 | | 1/2012 | Sos |

FOREIGN PATENT DOCUMENTS

WO   WO201206851   8/2011

* cited by examiner

*Primary Examiner* — Melanie R Tyson
(74) *Attorney, Agent, or Firm* — Brinks Gilson & Lione

(57) ABSTRACT

The present disclosure describes filter devices for deployment to body vessels where clots or emboli may need to be captured, particularly the vena cava. The filter device is of a spiral construction, having a first loop and a second loop, with a helical portion extending helically therebetween. The first and second loops assist in the filter being self-centering within a body vessel. A method of making a filter device is also disclosed.

17 Claims, 4 Drawing Sheets

SELF-CENTERING SPIRAL FILTER

BACKGROUND

The present invention relates to medical devices. More particularly, the invention relates to a filter that can be percutaneously placed in a blood vessel, such as the vena cava of a patient, to capture clots.

Filtering devices are widely utilized for protection against potential pulmonary thromboembolism (also referred to as PE) in at-risk patients. A need for filtering devices can arises in for example trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Filtering devices are either permanent or retrievable implants. A retrievable implant may be desirable so that a filtering device does not remain implanted in the patient for life, even though the condition or medical problem that required the device has passed. In more recent years, filters have also been used or considered prophylactically in preoperative patients and in patients predisposed to thrombosis which places the patient at risk for pulmonary embolism.

Currently available vena cava filters generally include a number of struts formed from individual pieces of wire arranged to give the filter its shape and collected at one end by a separate piece that gathers the ends of the struts together, such as a collet, a bushing, or a sleeve, generally referred to as a hub. Although these devices are effective, their construction could be simplified.

Moreover, although spiral-shaped filters are known, many of these suffer from low compressibility, and lack resistance to stress caused by compression from other portions of the body. Finally, some filters are susceptible to tilting or becoming off-center during deployment.

There is a need for filter devices which are simple to make and provide geometries that are efficacious for capturing emboli and clots.

BRIEF SUMMARY

In one aspect, the present disclosure provides a filter device for implantation into a body vessel, the device having a first loop having a first radius and a second loop having a second radius, at least one of the first loop and the second loop being arcuately disposed about a longitudinal axis of the filter; and a helical portion helically extending from the first loop to the second loop and comprising a plurality of turns, each turn having a radius of curvature increasing in the longitudinal direction from the first loop to the second loop, the filter being movable between a collapsed configuration and an expanded configuration. At least one of the first loop, the second loop, and at least one turn of the helical portion are aligned at an angle of less than 90 degrees relative to the longitudinal axis when in the expanded configuration.

In another aspect, the present disclosure describes a filter device for implantation into a body vessel, the device defining a longitudinal axis therethrough and including a first wire loop having a first radius measured from the longitudinal axis and having a first stiffness. The device also includes a second wire loop having a second radius measured from the longitudinal axis and having a second stiffness, at least one of the first loop and the second loop being arcuately disposed about a longitudinal axis of the filter. The device may include a helical portion helically extending from the first loop to the second loop and comprising a plurality of turns, each turn having a radius of curvature increasing in the longitudinal direction from the first loop to the second loop, the helical portion having a stiffness greater than the greater of the first stiffness and the second stiffness. The filter may be movable between a collapsed configuration and an expanded configuration. At least one of the first loop, the second loop, and at least one turn of the helical portion are aligned at an angle of less than 90 degrees relative to the longitudinal axis when in the expanded configuration.

Further objects, features, and advantages of the present invention will become apparent from consideration of the following description and the appended claims when taken in connection with the accompanying drawings.

BRIEF DESCRIPTION OF THE DRAWINGS

The drawings are purely schematic illustrations of various aspects of the invention and are not necessarily to scale, unless expressly stated.

DETAILED DESCRIPTION OF THE DRAWINGS

While the present invention has been described in terms of certain preferred embodiments, it will be understood that the invention is not limited to the disclosed embodiments, as those having skill in the art may make various modifications without departing from the scope of the following claims.

The terms "substantially" or "about" used herein includes variations in the recited characteristic or quantity that are functionally equivalent to the quantity recited, such as an amount that is equivalent to the quantity recited for an intended purpose or function. In the case of a numerical quantity, the terms "substantially" or "about" shall mean a range consisting of a value 20% less than the recited value to a value 20% greater than the recited value, inclusive.

As used herein, the terms "upstream" and "downstream" particularly refer to the direction of blood flow through a vessel. Blood flows from upstream to downstream. Reference made to an upstream or downstream end or portion of a filter device is done with reference to the deployed configuration of the device, with blood moving from the upstream end toward the downstream end of the device when the device has been deployed to a blood vessel.

As used herein, the terms "expanded configuration" and "deployed configuration" are to be understood as substantially interchangeable with regard to the shape of a filter device. Typically, the expanded configuration and the deployed configuration are substantially identical; "expanded" being used to describe the device when it has been shaped out of its flat configuration but not necessarily deployed to a body vessel, and "deployed" being used to describe a device which is resident in a blood vessel. A person of skill in the art will recognize that any dissimilarity between the expanded configuration and the deployed configuration will arise from the constraint applied by the wall of the vessel to which the filter device has been deployed.

Figure 1:
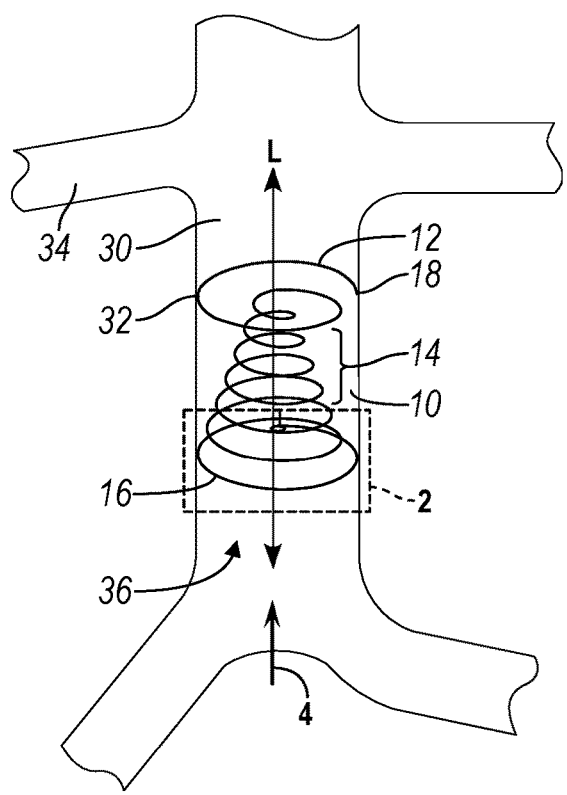
FIG. 1 is a cutaway view of a filter implanted in a body vessel in its expanded configuration or deployed configuration in accordance with one embodiment of the present invention.

FIG. 1 illustrates a first embodiment of a filter device 10 in accordance with the principles of the present disclosure. The filter device 10 is shown in its expanded configuration 36 and comprises a first loop 12, which extends from first end 18 radially around longitudinal axis L. First loop 12 is sized to contact the wall 32 of a vessel 30, such as a vena cava, in which it is to be implanted. In certain embodiments, the radius of curvature of the first loop 12 may be substantially equal to the radius of the vessel in which it is to be implanted. In another embodiment, a radius of curvature of the first loop 12 may exceed the radius of the vessel in which it is to be deployed, with the first loop 12 obligately deployed at an angle to the longitudinal axis of the vessel.

The filter 10 includes a spiral portion or helical portion 14 attached to and extending longitudinally from the first loop 12. The helical portion 14 includes a plurality of turns which extend radially around the longitudinal axis L, with the turns progressively increasing in the radial dimension in the longitudinal direction. In one embodiment, each successive turn has a greater diameter than one which is closer to the first loop 12. However, in other embodiments it may be possible to have consecutive turns of substantially the same diameter, while still having other turns that increase in diameter such that the overall conical shape of the helical portion 14 is maintained. The radius of curvature of the loops increases in the longitudinal direction away from the first loop 12.

The turns of the helical portion 14 may be spaced substantially equally away from one another in the longitudinal direction in one embodiment. In another embodiment, the turns of the helical portion 14 may be spaced at varied distances from one another in the longitudinal direction. In certain embodiments, it may be desirable for the helical portion 14 to take on a substantially conical or funnel shape to assist in filtering of blood. The filter 10 is designed to allow blood to flow through and minimizes the chances that clotting will occur by disrupting the dynamics of the flow.

In certain embodiments, the helical portion 14 may comprise a drug-eluting coating for delivery of a therapeutic agent to the vessel 30. The drug may be, for example, an anticoagulant, a chemotherapeutic, or any other class of at least one molecule that might be helpful to the patient being treated.

Figure 2:
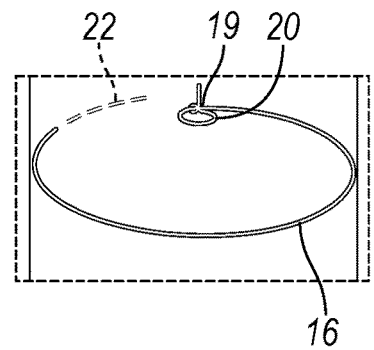
FIG. 2 is a close-up view of the anchoring hook and retrieval loop of the filter device of FIG. 1.

The helical portion 14 continues to extend until it terminates at, or incident with, second loop 16. Second loop 16 extends radially around longitudinal axis L and terminates at second end 19. Optionally, and as shown in FIG. 2, a retrievable loop 20 may be formed at second end 19 of the second loop 16. Further, an optional anchoring hook 22 or barb may be formed at second end 19 of the second loop 16 in order to keep the device positioned at the desired position within a vessel 30. The overall spiral shape of the filter 10 minimizes the chances that any component of the filter besides the optional anchoring hook 22 will penetrate the wall of a vessel in which it is implanted. This, in turn, extends the effective useful lifetime of the filter.

In certain aspects, the device has a first loop which is a primary loop with a primary radius. The device may also have a helical portion comprising a plurality of turns, each turn having a radius of curvature increasing and extending in the longitudinal direction from the primary loop and terminating with a second loop which is a secondary loop having a secondary radius; where the primary or secondary loop are arcuately disposed about a longitudinal axis of the filter. The filter may be movable between a collapsed configuration and an expanded configuration.

In other embodiments, the first loop 12 may be provided with a retrieval loop, an anchoring hook, or both. This may be in addition to the hook and/or retrieval loop of the second loop, such that bidirectional retrieval of the filter 10 is possible, or it may be provided only at one end or the other. In certain embodiments, no retrieval loop is provided. In other embodiments, no anchoring hook is present. In one embodiment, the device 10 lacks a retrieval loop and lacks an anchoring hook.

Second loop 16 may be sized to contact the wall 32 of the vessel 30 in which it is to be implanted. In certain embodiments, the radius of curvature of the second loop 16 may be substantially equal to the radius of the vessel in which it is to be implanted. In another embodiment, a radius of curvature of the second loop 16 may exceed the radius of the vessel in which it is to be deployed, with the second loop 16 obligately deployed at an angle to the longitudinal axis of the vessel.

In one embodiment, a self-expanding intravascular filter in accordance with the principles of the present disclosure can be made of a single, monolithic length of wire. In some embodiments, the wire may be made of a shape memory material. One example of a shape memory material is a shape memory metal, in particular a class of nickel-titanium alloys, including those marketed under the name NITINOL. Such alloys are known for their shape memory and pseudoelastic properties. As a shape memory material, such a nickel-titanium alloy is able to undergo a reversible thermoelastic transformation between certain metallurgical phases. In another embodiment, the shape memory or superelastic alloy may be an alloy of cobalt and chromium.

A device made from a shape memory material, in some embodiments a nickel-titanium alloy or a cobalt-chromium alloy, can be heat set to retain its shape after implantation. In one embodiment, the device may have a remembered state of well below body temperature such that at body temperature it returns to its original shape. In one example, the temperature may be about ten to about fifteen degrees Celsius. An elastic metal such as a cobalt-chromium alloy may have good fatigue probabilities and desirable elastic performance while deployed. However, other metals may also be employed.

In another embodiment, a filter device may be made of a stainless steel, such as stainless steel 304, which may take on the appropriate shape due to the spring-like overall configuration of the device.

The device in certain embodiments may be of unitary construction. In one sense, a device of unitary construction is made of a single piece of precursor material, such as a single length of wire. Specifically, a wire of a shape-memory metal such as a nickel-titanium alloy may be wound about a mandrel and heat set to yield the filter device. Unitary construction minimizes the complications in manufacture that derive from joining by soldering, welding, or using another method to connect separate parts into a unit. As used herein, the term "unitary" means that the device is made of a single piece which has not been joined to another piece.

However, in other embodiments, it may be desired to make certain portions of the device from a first material having specific desirable properties, and other portions of the device from a second material having different desirable properties. For instance, the first loop 12 and the second loop 16 may be made of a first relatively stiff material in order to achieve centering of the device in the vessel, and the helical portion 14 may be made of a relatively less stiff second material. In such a case, the material of the first loop 12 may be the same as the material of the second loop 16, or may differ from that of the second loop 16. In another embodiment, the wire may be made with a different thickness, with at least one of the first or primary loop 12 and the second or secondary loop 16 being thicker than the wire of the helical portion, thus making a device with stiffer elements at the ends to support the device in the vessel.

The device may, optionally, further incorporate radiopaque markers to assist a physician with placement in the body. Many suitable radiopaque materials are known and any of these may be selected for use with a device of the present disclosure. The radiopaque markers may be made of materials including gold, palladium, tantalum, platinum, and biocompatible alloys of any of these materials.

Figure 3A:
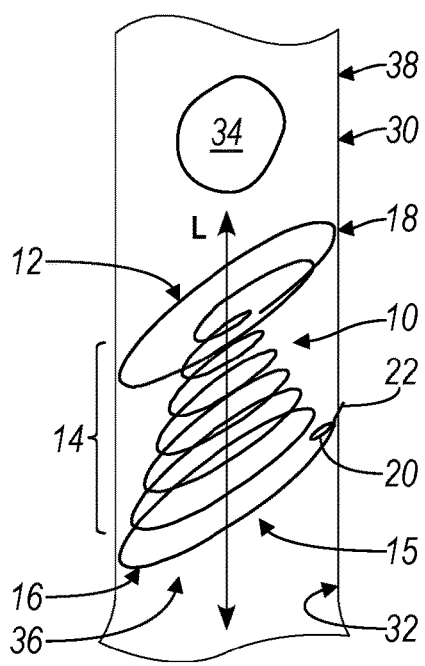
FIG. 3A is a side view of the filter device of FIGS. 1 and 2 in its expanded or deployed configuration in an uncompressed body vessel.

Turning now to FIG. 3A, a view of the filter 10 as deployed in vessel 30 in FIG. 1 is shown. This view is rotated approximately 90 degrees about the longitudinal axis L. As can be seen in this view, the first loop 12, second loop 16, and the turns of helical portion 14 are disposed at an acute angle relative to the longitudinal axis L. This angle gives the filter a slanted aspect.

The vessel in FIG. 3A is shown in an uncompressed state 38. However, blood vessels routinely endure compressive stress from normal body motions. This is particularly true of the vena cava, which may experience compressive stress from the lungs. During inhalation, the vena cava may be compressed. Since humans inhale and exhale numerous times every minute, this repetitive stress can put a strain on a device placed in the vena cava.

Figure 3B:
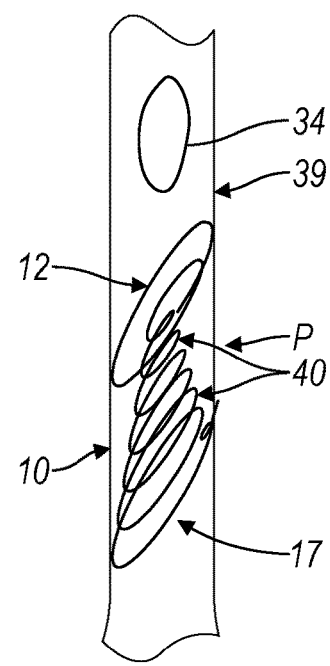
FIG. 3B is a side view of the filter device of FIG. 3A when the vessel in which it is implanted is compressed.

As depicted in FIG. 3B, the vessel 30 is now enduring a compressive pressure P, created a compressed vessel 39. The slanted aspect of the device allows for minimal disruption of the overall shape of the device, and minimizes stress and strain on the device 10. In some embodiments, the first loop 12 is slanted. In other embodiments, the second loop 16 is slanted. In other embodiments, the turns of the helical portion 14 are slanted relative to longitudinal axis L. Any combination of the preceding slanting arrangements is possible. When an element is slanted, it may make at least one angle of about 10 degrees to about 50 degrees relative to the longitudinal axis L, or more particularly about 30 degrees to about 45 degrees.

Figure 4:
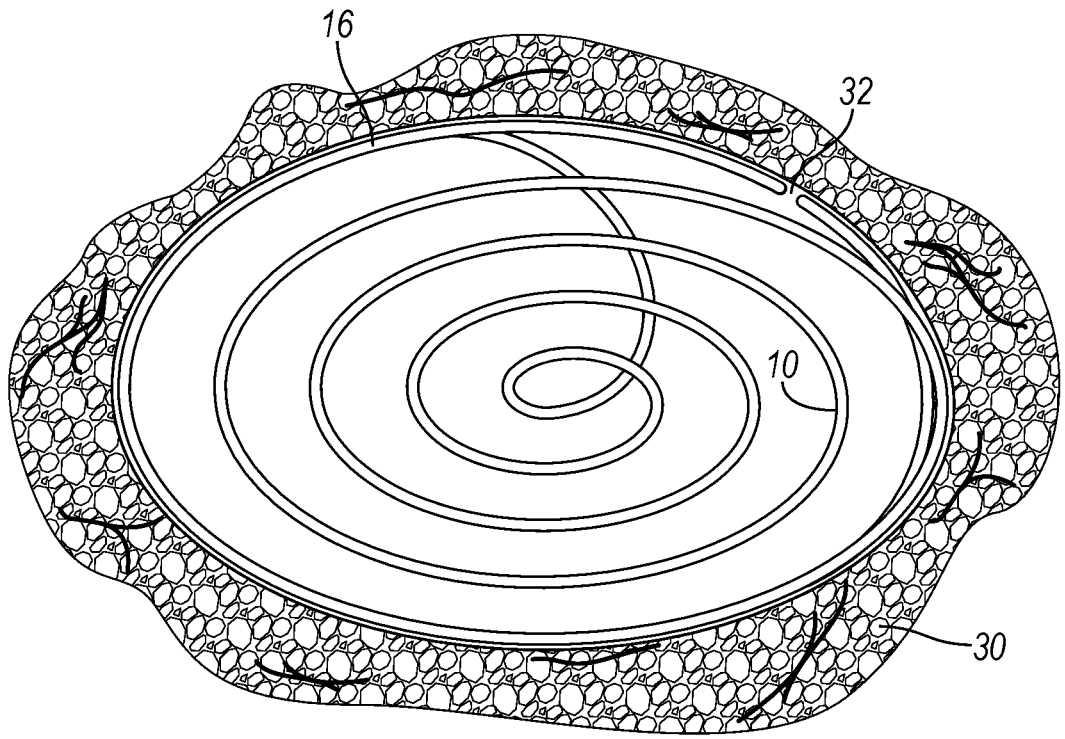
FIG. 4 is a view of the filter device of FIG. 1 implanted in a body vessel taken along the longitudinal axis of the device and of the vessel.

The filtering capacity of the device 10 is demonstrated by the end view as shown in FIG. 4. The turns of helical portion 14, which successively increase in radius of curvature in the longitudinal direction between first loop 12 and second loop 16, fill the lumen of the vessel 30, allowing blood to flow through and disrupting said flow to minimize clotting. The first loop 12 and the second loop 16 contact vessel wall 32, securing the device and centering it within the vessel 30.

Figure 5:
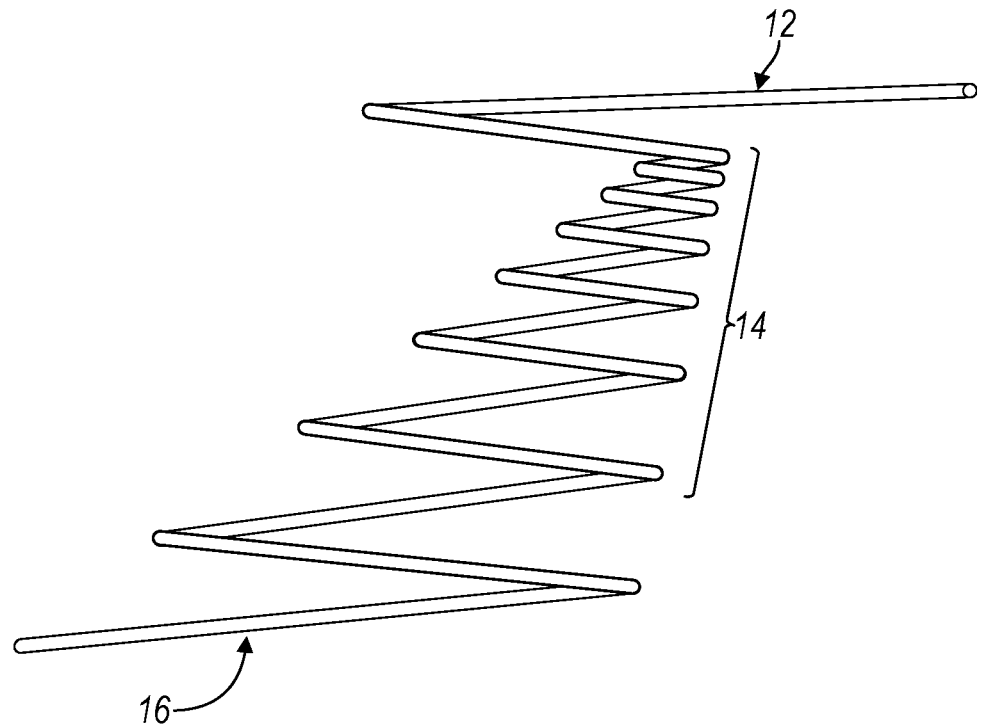
FIG. 5 is a side view of the device of FIG. 1 wherein the device is not implanted in a vessel.

To demonstrate the bias of the filter 10 to the angled configuration, the filter 10 is illustrated in FIG. 5 not implanted into a body vessel, but rather extracorporeally, such as standing on a flat surface. Rather than collapsing into substantially concentric turns as would be expected in an unslanted spiral device, the turns of helical portion 14 have more of an off-center, stacked configuration, with one edge of each of the turns of the filter substantially aligned vertically.

Figure 6:
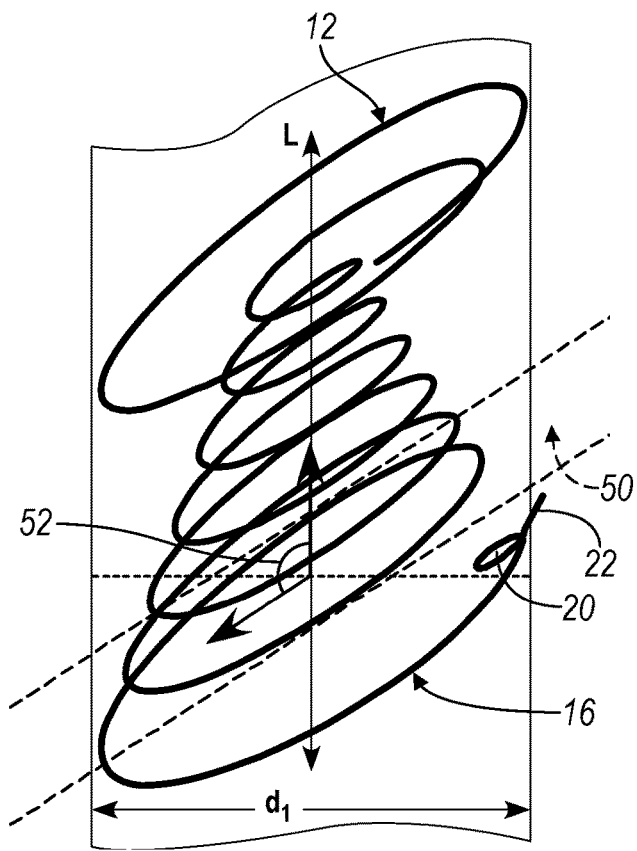
FIG. 6 is a side view of a filter device in its expanded or deployed configuration in an uncompressed body vessel according to one aspect of the present disclosure.
Figure 7:
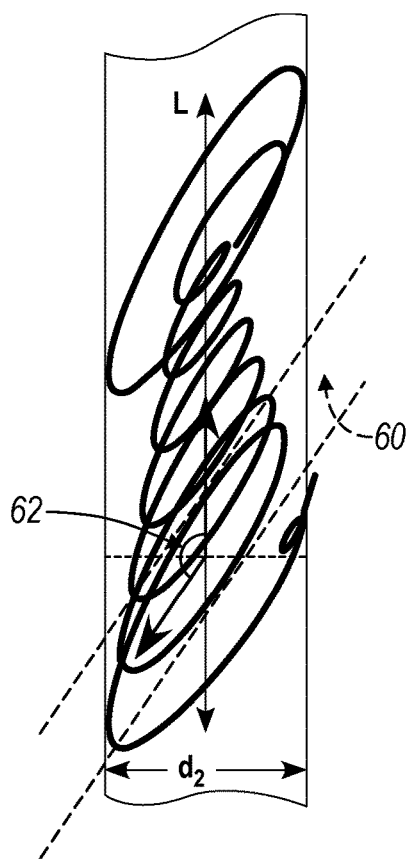
FIG. 7 is a side view of a filter device in its expanded or deployed configuration in a compressed body vessel according to one aspect of the present disclosure.
Figure 8:
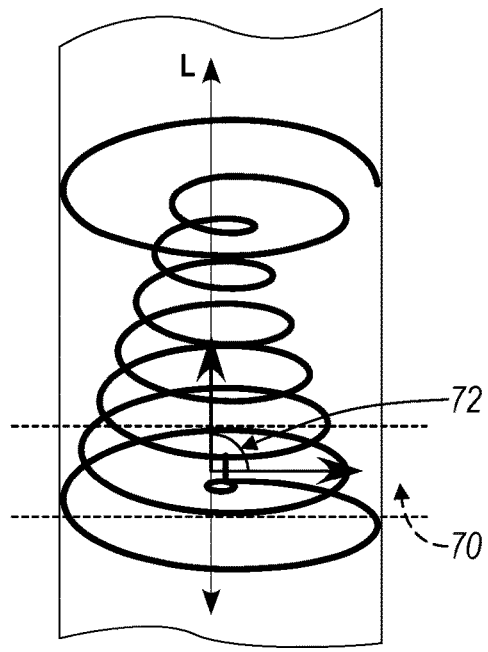
FIG. 8 is a side view of a prior art filter device deployed within a body vessel.

FIGS. 6 and 7 further demonstrate in a geometric sense how the slant of the turns of the helical portion 14, first loop 12, and second loop 16, may act in response to compression of a vessel. For example, FIG. 6 shows a filter 10 deployed in uncompressed vessel 30 having a diameter $d_1$. A plane 50 drawn through a turn of helical portion 14 makes an angle 52 with the longitudinal axis L. When the vessel is compressed to a smaller diameter $d_2$ as in FIG. 7, plane 60 makes a larger obtuse (and therefore smaller acute) angle with the longitudinal axis L. FIG. 8 illustrates a prior art filter that is not biased to have a slant. In this case, whether the vessel is compressed or uncompressed, the plane 70 lies at a substantially right angle 72 to the longitudinal axis L, causing the filter to be subject to relatively higher amount of stress during its lifetime in the blood vessel.

A filter as disclosed herein may be used with many existing delivery systems as are known in the art. Particularly when a device is made of an elastic metal such as a cobalt-chromium alloy, or because of the spring-like shape of the spiral filter, the final dimensions of the device are determined by the remembered state and not dependent upon manipulating the delivery system to crimp or otherwise modify the device as it is being loaded.

Figure 9:
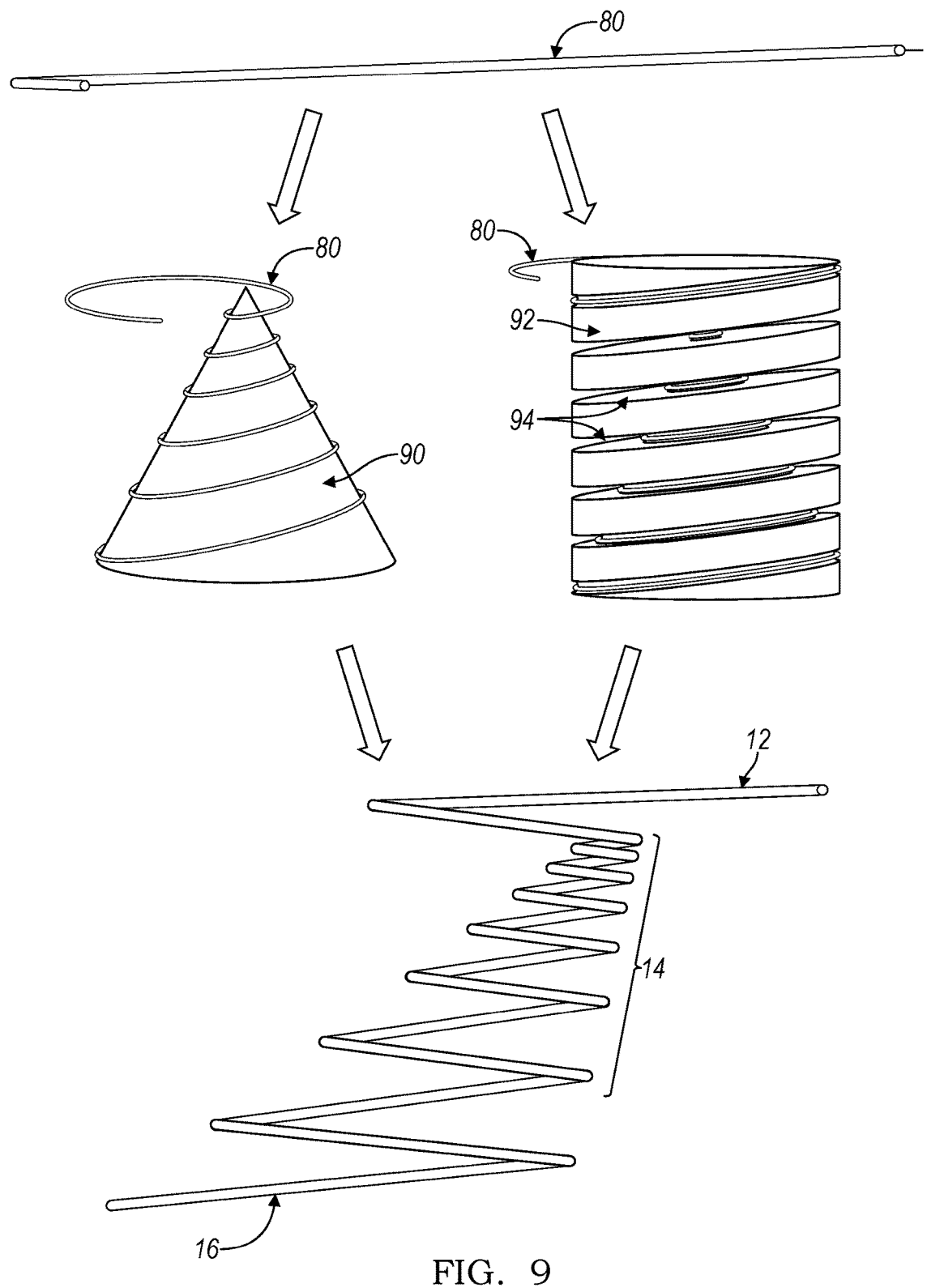
FIG. 9 is a schematic view of methods of making a filter according to the principles of the present disclosure using a conical or a tubular mandrel to achieve a slanted spiral shape.

A device in accordance with the principles of the present disclosure may be made according to a series of steps, as illustrated in FIG. 9. As mentioned previously, a single, monolithic, length of wire 80 may be precisely wound and shaped to generate the overall shape of the filter device.

In one embodiment, the wire 80 may be wrapped about a substantially conical or frusto-conical mandrel 90. The wire is wound in an angled fashion around the outer surface of the mandrel to form what will become the helical portion, and then heat set. The first loop and second loop may be heat set together with or separately from the helical portion of the device.

In another embodiment, the mandrel 92 may be a cylindrical or tubular structure that has a groove 94 running around it, creating a track in which to place the wire 80. The groove 94 from one end longitudinally to the opposite end of mandrel 92 increases in depth so that the radius of curvature of the windings decreases in the longitudinal direction. The angle of the grooves allows for formation of the helical portion of the device.

A method of using a filter device as described in the instant disclosure can include a number of different steps. In one step, the filter device may be compressed to a compressed state and loaded into a delivery assembly. The delivery assembly may be introduced to the body percutaneously, and the device delivered, such as by a pusher, into the lumen of the body vessel, in one embodiment the vena cava, more particularly the inferior vena cava. The filter device, upon deployment, will anchor against the vessel wall as it is deployed from the delivery assembly as it returns to its remembered, unconstrained state. Delivery may be guided by imaging which may optionally include monitoring of one or more radiopaque portions included on the device. After the device has been secured within the body vessel, the delivery assembly is removed from the patient. The device may optionally be retrieved after a practitioner is satisfied with the progression of treatment.

While the present invention has been described in terms of certain preferred embodiments, it will be understood that the invention is not limited to the disclosed embodiments, as those having skill in the art may make various modifications without departing from the scope of the following claims.

The invention claimed is:

1. A filter for implantation in a body lumen, the filter comprising:
   a first loop having a first radius;
   a second loop having a second radius, at least one of the first loop and the second loop being arcuately disposed about a longitudinal axis of the filter; and
   a helical portion helically extending from the first loop to the second loop and comprising a plurality of turns, each turn having a radius of curvature increasing in the longitudinal direction from the first loop to the second loop;
   wherein the filter is movable between a collapsed configuration and an expanded configuration, and
   wherein at least one of the first loop, the second loop, and at least one turn of the helical portion are aligned at an angle of between 10 degrees and 50 degrees relative to the longitudinal axis when in the expanded configuration.

2. The filter of claim 1, wherein at least one of the first loop and the second loop are aligned at an angle of between 10 degrees and 50 degrees relative to the longitudinal axis when in the expanded configuration.

3. The filter of claim 1, wherein at least one turn of the helical portion is aligned at an angle of between 10 degrees and 50 degrees relative to the longitudinal axis when in the expanded configuration.

4. The filter of claim 1, wherein the first loop, the second loop, and at least one turn of the helical portion are each aligned at angles of between 10 degrees and 50 degrees relative to the longitudinal axis when in the expanded configuration.

5. The filter of claim 1, wherein the first loop, the second loop, and each turn of the helical portion are each aligned at angles of between 10 degrees and 50 degrees relative to the longitudinal axis when in the expanded configuration.

6. The filter of claim 1, wherein the angle is between about 30 degrees and about 45 degrees.

7. The filter of claim 1, wherein the first radius is substantially equal to the second radius.

8. The filter of claim 1 further comprising a retrieval loop connected to the second loop.

9. The filter of claim 1 further comprising at least one anchoring hook connected to at least one of the first loop and the second loop.

10. The filter of claim 1, wherein the filter comprises a wire comprising a shape memory alloy.

11. The filter of claim 10, wherein the shape memory alloy comprises nickel and titanium.

12. The filter of claim 1, wherein at least a portion of the helical portion comprises a drug-eluting coating.

13. A filter for implantation in a body lumen, the filter defining a longitudinal axis therethrough and comprising:
    a first wire loop having a first radius measured from the longitudinal axis and having a first stiffness;
    a second wire loop having a second radius measured from the longitudinal axis and having a second stiffness, at least one of the first wire loop and the second wire loop being arcuately disposed about a longitudinal axis of the filter; and
    a helical portion helically extending from the first wire loop to the second wire loop and comprising a plurality of turns, each turn having a radius of curvature increasing in the longitudinal direction from the first wire loop to the second wire loop, the helical portion having a stiffness greater than the greater of the first stiffness and the second stiffness;
    wherein the filter is movable between a collapsed configuration and an expanded configuration, and
    wherein at least one of the first wire loop, the second wire loop, and at least one turn of the helical portion are aligned at an angle of between 10 degrees and 50 degrees relative to the longitudinal axis when in the expanded configuration.

14. The filter of claim 13, wherein the first wire loop and the second wire loop are aligned at an angle of between 10 degrees and 50 degrees relative to the longitudinal axis when in the expanded configuration.

15. The filter of claim 13, wherein at least one turn of the helical portion is aligned at an angle of between 10 degrees and 50 degrees relative to the longitudinal axis when in the expanded configuration.

16. The filter of claim 13, wherein the angle is between about 30 degrees and about 45 degrees.

17. The filter of claim 13, wherein the first wire loop and the second wire loop comprise a shape memory alloy.

* * * * *